United States Patent [19]

Germond et al.

[11] Patent Number: 5,683,890
[45] Date of Patent: Nov. 4, 1997

[54] **BACTERIOCINS FROM *STREPTOCOCCUS THERMOPHILUS***

[75] Inventors: Jacques Edouard Germond, Crissier; Olivier Marciset, Lausanne; Beat Mollet, Mollie-Margot, all of Switzerland

[73] Assignee: Nestec S.A., Vevey, Switzerland

[21] Appl. No.: 428,091

[22] PCT Filed: Aug. 24, 1994

[86] PCT No.: PCT/EP94/02805
§ 371 Date: May 1, 1995
§ 102(e) Date: May 1, 1995

[87] PCT Pub. No.: WO95/06736
PCT Pub. Date: Mar. 9, 1995

[30] Foreign Application Priority Data

Sep. 3, 1993 [CH] Switzerland .............. 2628/93

[51] Int. Cl.[6] .............. C12P 21/02; C07H 21/04; C07K 14/315; A23C 9/123
[52] U.S. Cl. .............. 435/69.1; 426/34; 435/71.3; 435/253.4; 435/885; 530/300; 536/23.1; 536/23.7
[58] Field of Search .............. 435/69.1, 71.1, 435/71.3, 253.4, 320.1, 885; 536/23.1, 23.7, 24.1; 530/300; 426/34, 36, 55, 61, 43

[56] References Cited

U.S. PATENT DOCUMENTS 5,338,682   8/1994   Sasaki et al. .............. 435/253.4
5,482,723   1/1996   Sasaki et al. .............. 426/43

FOREIGN PATENT DOCUMENTS 443 543 A3   8/1991   European Pat. Off. .

OTHER PUBLICATIONS

Smaczny, T. et al.; "Säuerungstörungen in der Joghurt–, Biohurt –und Biogarde –Produktion, bedingt durch Bacteriocn und Bakteriophagen von *Streptococcus thermophilus*"; Deutsche Molkerei–Zeitung, vol. 105, No. 15, 1984, pp.460–464.

Ward, D. J. et al.; "Bacteriocin production in *Streptococcus thermophilus*"; Abstracts of the Annual Meeting of the American Society for Micorbiology, May 1993, Washington U.S., p. 344.

Muriana et al. "Cloning, Phenotypic Expression & DNA Sequence of the Gene for Lactacin F..." J Bacteriol. 173(5) 1779–1788 1991.

*Primary Examiner*—Nancy Degen
*Attorney, Agent, or Firm*—Pennie & Edmonds

[57] ABSTRACT

The invention relates to two new *Streptococcus thermophilus* bacteriocins having the amino acid sequences SEQ ID NO: 1 and SEQ ID NO: 2, the signal peptides of these two bacteriocins, the nucleotide sequences encoding these bacteriocins especially an operon encoding the bacteriocins having the sequence SEQ ID NO: 3, the strains producing at least one of these bacteriocins especially the strain CNCM I-1351, a method for producing a supernatant extract comprising at least one of these two bacteriocins, and use of these bacteriocins in the preparation of food products, especially cheeses and acidified milks, and cosmetic products as active agent against pathogens.

7 Claims, No Drawings

5,683,890

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
　　　　　　　　( A ) LENGTH: 62 amino acids
　　　　　　　　( B ) TYPE: amino acid
　　　　　　　　( D ) TOPOLOGY: linear ( i i ) MOLECULE TYPE: protein ( v i ) ORIGINAL SOURCE:
　　　　　　　　( A ) ORGANISM: Streptococcus thermophilus
　　　　　　　　( B ) STRAIN: CNCM I-1351

( x i ) SEQUENCE DESCRIPTION: SEQ ID NO:1:

```
Tyr Ser Gly Lys Asp Cys Leu Lys Asp Met Gly Gly Tyr Ala Leu Ala
 1               5                  10                  15

Gly Ala Gly Ser Gly Ala Leu Trp Gly Ala Pro Ala Gly Gly Val Gly
                20                  25                  30

Ala Leu Pro Gly Ala Phe Val Gly Ala His Val Gly Ala Ile Ala Gly
            35                  40                  45

Gly Phe Ala Cys Met Gly Gly Met Ile Gly Asn Lys Phe Asn
        50                  55                  60
```

( 2 ) INFORMATION FOR SEQ ID NO:2:

( i ) SEQUENCE CHARACTERISTICS:
　　　　　　　　( A ) LENGTH: 43 amino acids
　　　　　　　　( B ) TYPE: amino acid
　　　　　　　　( D ) TOPOLOGY: linear ( i i ) MOLECULE TYPE: protein ( v i ) ORIGINAL SOURCE:
    ( A ) ORGANISM: Streptococcus thermophilus
    ( B ) STRAIN: CNCM I-1351

( x i ) SEQUENCE DESCRIPTION: SEQ ID NO:2:

```
Gln Ile Asn Trp Gly Ser Val Val Gly His Cys Ile Gly Gly Ala Ile
 1               5                  10                      15

Ile Gly Gly Ala Phe Ser Gly Gly Ala Ala Ala Gly Val Gly Cys Leu
            20                  25                  30

Val Gly Ser Gly Lys Ala Ile Ile Asn Gly Leu
            35                  40
```

( 2 ) INFORMATION FOR SEQ ID NO:3:

( i ) SEQUENCE CHARACTERISTICS:
       ( A ) LENGTH: 770 base pairs
       ( B ) TYPE: nucleic acid
       ( C ) STRANDEDNESS: single
       ( D ) TOPOLOGY: linear ( i i ) MOLECULE TYPE: DNA (genomic)

( v i ) ORIGINAL SOURCE:
       ( A ) ORGANISM: Streptococcus thermophilus
       ( B ) STRAIN: CNCM I-1351

( i x ) FEATURE:
       ( A ) NAME/KEY: CDS
       ( B ) LOCATION: 221..475

( i x ) FEATURE:
       ( A ) NAME/KEY: sig_peptide
       ( B ) LOCATION: 221..289

( i x ) FEATURE:
       ( A ) NAME/KEY: mat_peptide
       ( B ) LOCATION: 290..475
       ( D ) OTHER INFORMATION: /function= "encodes for
             thermophiline 1"

( i x ) FEATURE:
       ( A ) NAME/KEY: CDS
       ( B ) LOCATION: 495..686

( i x ) FEATURE:
       ( A ) NAME/KEY: sig_peptide
       ( B ) LOCATION: 495..557

( i x ) FEATURE:
       ( A ) NAME/KEY: mat_peptide
       ( B ) LOCATION: 558..686
       ( D ) OTHER INFORMATION: /function= "encodes for
             thermophiline 2"

( x i ) SEQUENCE DESCRIPTION: SEQ ID NO:3:

```
AATGGCACGA ACGTCCTGAA TGGTTAAAAG ATATTTCGGA TCTTCCTAAA AAATACATAC        60

TGAACGGTCG CTTTCCCTTC TTGAATGGTA AAATTTTCCC ATTAGGAAAG TTAAATGACT       120

GTTCAAGAAA TGGGGAAATT ATTTTTTGAA GTAGTGCTAT ACTAGACTTG TCAAGGTTGC       180

AACCCGACAA AATAAAAATA TTAGGTAGGA GATATTTACA ATG AAT ACA ATA ACT        235
                                             Met Asn Thr Ile Thr
                                             -23             -20

ATT TGT AAA TTT GAT GTT TTA GAT GCT GAA CTT CTT TCG ACA GTT GAG        283
Ile Cys Lys Phe Asp Val Leu Asp Ala Glu Leu Leu Ser Thr Val Glu
        -15                 -10                 -5

GGT GGA TAC TCT GGT AAG GAT TGT TTA AAA GAC ATG GGA GGA TAT GCA        331
Gly Gly Tyr Ser Gly Lys Asp Cys Leu Lys Asp Met Gly Gly Tyr Ala
            1               5                   10

TTG GCA GGA GCT GGA AGT GGA GCT CTG TGG GGA GCT CCA GCA GGA GGT        379
```

```
        Leu Ala Gly Ala Gly Ser Gly Ala Leu Trp Gly Ala Pro Ala Gly Gly
        15                  20                  25                  30

GTT GGA GCA CTT CCA GGT GCA TTT GTC GGA GCT CAT GTT GGG GCA ATT         427
        Val Gly Ala Leu Pro Gly Ala Phe Val Gly Ala His Val Gly Ala Ile
                        35                  40                      45

GCA GGA GGC TTT GCA TGT ATG GGT GGA ATG ATT GGT AAT AAG TTT AAC         475
        Ala Gly Gly Phe Ala Cys Met Gly Gly Met Ile Gly Asn Lys Phe Asn
                    50                  55                  60

TAAGGAAGGA GTTATATC ATG AAG CAG TAT AAT GGT TTT GAG GTT CTA CAT         527
                            Met Lys Gln Tyr Asn Gly Phe Glu Val Leu His
                            -21 -20                     -15

GAA CTT GAC TTA GCA AAT GTA ACT GGC GGT CAA ATT AAT TGG GGA TCA         575
        Glu Leu Asp Leu Ala Asn Val Thr Gly Gly Gln Ile Asn Trp Gly Ser
        -10             -5                      1                   5

GTT GTA GGA CAC TGT ATA GGT GGA GCT ATT ATC GGA GGT GCA TTT TCA         623
        Val Val Gly His Cys Ile Gly Gly Ala Ile Ile Gly Gly Ala Phe Ser
                        10                  15                  20

GGA GGT GCA GCG GCT GGA GTA GGA TGC CTT GTT GGG AGC GGA AAG GCA         671
        Gly Gly Ala Ala Ala Gly Val Gly Cys Leu Val Gly Ser Gly Lys Ala
                    25                  30                  35

ATC ATA AAT GGA TTA TAAAAGTCTT TTATCGCTTT TATTATTCAT AATTCCCCTT         726
        Ile Ile Asn Gly Leu
                    40

GTAGTTATAC TAATCGTTCT TCGAAAGAAT AATCAGAAAC TAAT                        770
```

( 2 ) INFORMATION FOR SEQ ID NO:4:

( i ) SEQUENCE CHARACTERISTICS:
        ( A ) LENGTH: 85 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Asn Thr Ile Thr Ile Cys Lys Phe Asp Val Leu Asp Ala Glu Leu
-23         -20             -15                 -10

Leu Ser Thr Val Glu Gly Gly Tyr Ser Gly Lys Asp Cys Leu Lys Asp
            -5                  1                   5

Met Gly Gly Tyr Ala Leu Ala Gly Ala Gly Ser Gly Ala Leu Trp Gly
10                  15                  20                  25

Ala Pro Ala Gly Gly Val Gly Ala Leu Pro Gly Ala Phe Val Gly Ala
                30                  35                  40

His Val Gly Ala Ile Ala Gly Gly Phe Ala Cys Met Gly Gly Met Ile
                45                  50                  55

Gly Asn Lys Phe Asn
            60
```

( 2 ) INFORMATION FOR SEQ ID NO:5:

( i ) SEQUENCE CHARACTERISTICS:
        ( A ) LENGTH: 64 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Lys Gln Tyr Asn Gly Phe Glu Val Leu His Glu Leu Asp Leu Ala
-21 -20                 -15                 -10

Asn Val Thr Gly Gly Gln Ile Asn Trp Gly Ser Val Val Gly His Cys
-5              1                   5                   10
```

```
Ile Gly Gly Ala Ile Ile Gly Gly Ala Phe Ser Gly Gly Ala Ala Ala
             15              20              25

Gly Val Gly Cys Leu Val Gly Ser Gly Lys Ala Ile Ile Asn Gly Leu
             30              35              40
```

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:6:

GA Y ATGGGNG GNTA Y GC                 17

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( x i ) SEQUENCE DESCRIPTION: SEQ ID NO:7:

GCTATNGCNC CNACGTG                 17

( 2 ) INFORMATION FOR SEQ ID NO:8:

( i ) SEQUENCE CHARACTERISTICS:
        ( A ) LENGTH: 128 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: Streptococcus thermophilus
        ( B ) STRAIN: CNCM I-1351

( x i ) SEQUENCE DESCRIPTION: SEQ ID NO:8:

```
GATTGTTTAA AAGACATGGG AGGATATGCA TTGGCAGGAG CTGGAAGTGG AGCTCTGTGG        60

GGAGCTCCAG CAGGAGGTGT TGGAGCACTT CCAGGTGCAT TTGTCGGAGC TCATGTTGGG       120

GCAATTGC                                                                128
```

BACTERIOCINS FROM *STREPTOCOCCUS THERMOPHILUS*

TECHNICAL FIELD

The subject of the present invention is two bacteriocins from *Streptococcus (S.) thermophilus*, a strain of *S. thermophilus* which produces these bacteriocins, a process for producing these bacteriocins from this strain, as well as uses of these bacteriocins and/or of this strain in the preparation of food products or cosmetic products.

STATE OF THE ART

A bacteriocin is an antibacterial substance or an agent which is active against bacteria comprising a protein portion which is involved in the antibacterial effect or antibiotic effect. A bacteriocin generally has a narrow activity spectrum or inhibition spectrum often limited to species close to the species of the bacterium which produces it.

Currently, four *S. thermophilus* bacteriocins are known.

The first has, in particular, a molecular weight of 10 to 20 kD, exhibits thermolability at 90° C. and sensitivity to pepsin (Smaczny et al., Deutsche Molkerei-Zeitung, 105: 15, 460–464, 1984).

The second, which is described mainly by its bacteria inhibition spectrum in EP 443543, has especially the capacity to inhibit the growth of bacteria of the genus Staphylococcus and Pseudomonas, and the inability to inhibit the growth of bacteria of the genus Lactococcus and Enterococcus, and of the species *Bacillus cereus*.

The third, which is described by Pulusani et al. (J. of Food Science, 44:2, 575–578, 1979), strongly inhibits Pseudomonas, is not sensitive to pepsin, and contains sugar residues.

Finally, the fourth, described by Gilano et al. (Microbiologie-Aliment-Nutrition, 8, 21–30, 1990), is not sensitive to pepsin, contains sugar residues and does not pass across a membrane with a porosity of 100 kD.

Now, *S. thermophilus* is of major importance in the food sector, being especially involved in the preparation of dairy products such as yogurts and some cheeses for example. Furthermore, very few bacteriocins exist which are active at the same time against Bacillus, Clostridium and Listeria. It may therefore be more useful, in other words there is a need for a broader range of bacteriocins produced by representatives of this species in order to have especially a broader antibacterial activity spectrum, in particular in the context of this type of product.

The aim of the present invention is to respond to this need.

SUMMARY OF THE INVENTION

One of the subjects of the present invention is the characterization of the amino acid sequence of two new *S. thermophilus* bacteriocins, as well as their signal peptide which permits their excretion.

The nucleotide sequences encoding these two bacteriocins are also another subject of the invention.

The *Streptococcus thermophilus* strains producing at least one of the bacteriocins according to the invention are also another subject of the invention, especially the strain CNCM I-1351 of *S. thermophilus* described below, which is capable of producing the two bacteriocins according to the invention.

The process for producing an extract of at least one bacteriocin according to the present invention is also another subject of the present invention.

Finally, the last subject of the present invention is the use of the bacteriocins according to the invention and the use of their nucleic sequence, as well as their signal sequence.

DETAILED DESCRIPTION OF THE INVENTION

A strain CNCM I-1351 of *S. thermophilus* was isolated from a fermented dairy product from Czechoslovakia and it was observed, surprisingly, that it has the remarkable property of inhibiting the growth of a broad range of bacteria. This strain was deposited on May 8, 1993, according to the Budapest Treaty, at the Collection Nationale de Cultures de Microorganismes, PASTEUR INSTITUTE, 25, Rue du Docteur Roux, F-75724 PARIS CEDEX 15, France where it was thus assigned the No. I-1351. Any and all restrictions on the availability to the public of the material so deposited will be irrevocably removed upon the granting of a patent for the present invention.

Details on this strain relating especially to its morphology, the fermentation of sugars and the like are given below:

Morphology:

Non-flagellated chain-forming cocci. No formation of spores.

Gram-positive microorganisms, catalase negative and facultative anaerobes.

Fermentation of sugars:

Production of lactic acid from D-glucose, lactose, sucrose, raffinose. No production of lactic acid from mannose, fructose, galactose.

Others:

Strain producing at least two bacteriocins, one protein for immunity to bacteriocins, and exopolysaccharides having texturizing properties.

The culture supernatant of the CNCM I-1351 strain therefore has a relatively broad anti-bacteria activity spectrum. Among the bacteria sensitive to this supernatant, there may be included *Streptococcus thermophilus*, *Lactococcus lactis*, *Lactococcus lactis* biovar *diacetylactis*, *Lactococcus cremoris*, *Enterococcus faecalis*, *Enterococcus faecium*, *Lactobacillus fermentum*, *Lactobacillus helveticus*, *Lactobacillus bulgaricus*, *Lactobacillus acidophilus*, *Lactobacillus brevis*, *Leuconostoc cremoris*, *Leuconostoc mesenteroides*, *Bifidobacterium breve*, *Bifidobacterium longum*, *Bifidobacterium bifidum*, *Bifidobacterium infantis*, Propionibacterium, *Listeria innocua*, *Listeria momocytogenes*, *Micrococcus varians*, and the spores and the vegetative cells of *Clostridium botulinum*, *Clostridium tyrobutyricum*, *Clostridium bifermentans*, *Clostridium sporogenes*, *Bacillus subtilis*, *Bacillus pumilus* and *Bacillus cereus*, for example (*Bactéries lactiques*, vol 1, 1994, Lorica edition).

It was then possible to isolate from this CNCM I-1351 strain two protein factors called bacteriocins, which are responsible for this antibacterial activity.

To this end, the first bacteriocin according to the invention which is named in this disclosure "thermophilin 1", has the sequence SEQ ID NO: 1 described in the sequence listing below.

Furthermore, it is possible to envisage that this bacteriocin may have an antibacterial activity having a broader or more specific spectrum for one genus or one bacterial species than that exhibited by thermophilin 1, when the latter has a sequence differing from the sequence SEQ ID NO: 1 in a substitution, a deletion and/or an insertion of at least one amino acid for example. Indeed, it is already known from EP 521240 that nisin Z has a more advantageous activity spectrum than nisin A, whereas it differs from nisin A only in a substitution of an amino acid.

That is why all the bacteriocins having a substitution, a deletion and/or an insertion of at least one amino acid in their original sequence SEQ ID NO: 1 can be considered as bacteriocins according to the present invention.

The second bacteriocin according to the invention, called in this disclosure "thermophilin 2", has the sequence SEQ ID NO: 2 described in the sequence listing below. It is also possible to envisage that this bacteriocin may have an antibacterial activity when it has a sequence which differs from the sequence SEQ ID NO: 2 by a substitution, a deletion and/or an insertion of at least one amino acid for example. To this end, all bacteriocins having at least one of the modifications described above in their original sequence SEQ ID NO: 2 can be considered as bacteriocins according to the present invention.

In addition, the nucleotide sequences encoding thermophilin 1 and thermophilin 2 are also another subject of the present invention because they can each be used to confer, by transformation, on bacteria, yeast or plants for example, a capacity to inhibit certain bacteria. These nucleotide sequences can thus be relatively variable because of the degeneracy of the genetic code, and may especially be comprised within an operon of the SNCM I-1351 strain having the nucleic sequence SEQ ID NO: 3 described in the sequence listing below.

In particular, it is possible to use the nucleic sequence comprising nucleotides 221 to 475 of the sequence SEQ ID NO: 3, which encodes thermophilin 1 with its signal peptide. However, it is more advantageous to use only the sequence encoding the signal peptide, from nucleotide 221 to 288 of the sequence SEQ ID NO: 3, to fuse it to a gene of interest, so as to be able to permit the excretion, by a *Streptococcus thermophilus* strain, of the protein encoded by this gene of interest. Likewise, it is more advantageous to use only the sequence encoding the excreted thermophilin 1, from nucleotide 289 to 475 of the sequence SEQ ID NO: 3, in order to be able to fuse it to a signal sequence in an expression plasmid, for example, so as to express it in a microorganism other than *S. thermophilus*.

Likewise, the nucleic sequence comprising nucleotides 495 to 686 of the sequence SEQ ID NO: 3, which encodes thermophilin 2 with its signal peptide, can be used. However, it is more advantageous to use only the sequence encoding the signal peptide, from nucleotide 495 to 557 of the sequence SEQ ID NO: 3, in order to be able to permit the excretion, by a *Streptococcus thermophilus* strain, of any protein fused to this peptide. Likewise, it is more advantageous to use only the sequence encoding the excreted thermophilin 2, from nucleotide 558 to 686 of the sequence SEQ ID NO: 3, in order to be able to fuse it to a signal sequence in an expression plasmid, for example, in order to express it in a microorganism other than *S. thermophilus*.

Finally, as it has been observed that certain *S. thermophilus* strains, other than the strain CNCM I-1351, exhibit an inhibition spectrum similar to that exhibited by the strain CNCM I-1351 and a resistance to the latter (especially the strains Sfi12 and 25 described below), it is highly probable that these strains can produce at least one of the bacteriocins of the present invention, at the same time as an immunity protein conferring this resistance. To this end, all the strains capable of producing at least one of the bacteriocins described above are included in the present invention.

In the process for producing an extract comprising at least one bacteriocin according to the present invention, an *S. thermophilus* strain which produces at least one of the bacteriocins is cultured in a medium and under conditions favorable to the growth of *S. thermophilus* until the medium contains $10^7$–$10^9$ microorganisms of the strain per ml, the culture obtained is centrifuged and then an extract of the supernatant comprising at least one of the bacteriocins is prepared.

To produce this extract, the *S. thermophilus* strain producing at least one of the bacteriocins according to the present invention, especially the strain CNCM I-1351 of *S. thermophilus*, can therefore be cultured in a medium and under conditions favorable to the growth of *S. thermophilus*. It can be cultured especially in an MSK medium (skimmed cow's milk supplemented with yeast extract) or in a HJ medium (cow's milk ultrafiltration permeate supplemented with yeast extract and soytone) for example. It is preferably cultured in a medium which is selective for Streptococcus, such as the M 17 medium described by P. E. Terzaghi et al., J. Appl. Microbiol., 29, 807–813 (1975), supplemented with 0.5–2% of a sugar which can be fermented by *S. thermophilus*, especially sucrose, lactose or glucose for example.

Such a medium can be prepared by mixing 95 ml of a basic medium and 5 ml of a solution containing 10 g of fermentable sugar per 100 ml of water, the solution of fermentable sugar and the basic medium having each been sterilized separately at 121° C. for 15 min and the basic medium having been prepared by dissolving the following components in 950 ml of boiling water:

| | |
|---|---|
| trypsin casein hydrolysate | 2.5 g |
| pepsin meat hydrolysate | 2.5 g |
| papain soya bean hydrolysate | 5.0 g |
| yeast extract | 2.5 g |
| meat extract | 5.0 g |
| beta-glycerophosphate | 19 g |
| Mg sulphate | 0.25 g |
| ascorbic acid | 0.5 g |

The strain can be cultured in the medium favourable for the growth of *S. thermophilus* at 37°–48° C., for 2–8 h for example, until the medium contains about $10^7$–$10^9$ microorganisms of the strain per ml, a value of about $10^8$ microorganisms/ml corresponding, on the one hand, to an optical density of the medium, measured at 600 nm ($OD_{600}$), of about 3.6 and, on the other hand, to the concentration reached in a cow's milk at the point where it coagulates under the effect of the acidification produced by the cultured strain.

To prepare a crude extract of the supernatant, it is possible to use any appropriate precipitation method such as precipitation with trichloroacetic acid, "salting out" or solvent precipitation for example. Preferably, in order to prepare this crude extract, the pH of the supernatant is adjusted to 1.0–2.0 with $H_3PO_4$, a precipitate is removed, and one or more successive precipitations are carried out with trichloroacetic acid each followed with resuspension in an aqueous suspension with trifluoroacetic acid.

Use of the bacteriocins and/or of a *Streptococcus thermophilus* strain which produces these bacteriocins according to the present invention is provided for in the preparation of food products or cosmetic products.

A culture of the *Streptococcus thermophilus* strain can be used in particular as starter in the preparation of cheeses, especially of cheeses of the mozzarella type (to avoid the holes produced by *Bacillus polymixa* whose spores survive the fermentation), of the Swiss type (such as Gruyère or Emmental, to combat contamination by *Clostridium tyrobutyricum*), of the vacherin type (to combat contamination by *Listeria monocytogenes*), and of the "séré" type (French name for soft or cream cheese), or in the preparation of acidified milks, especially of yogurt or of powdered milk for infant formulas, for example.

In particular, the *Streptococcus thermophilus* strain can be cultured in milk in combination with a *Lactobacillus bulgaricus* strain which is mildly sensitive to thermophilin (for example the strain YL5 described below), to avoid the post-acidification of the yogurt due to *L. bulgaricus*.

The bacteriocins, especially in the form of a crude or purified extract, or the strain can also be used as additive or active agent against pathogenic bacteria, especially in the preparation of meat products such as mousses, as active agent against the growth of clostridia spores, especially *Clostridium botulinum*, or in the preparation of creams or lotions, as active agent against pathogenic bacteria of the skin, or alternatively in the preparation of oral health products, as active agent against pathogenic bacteria of the buccal cavity, especially against *Streptococcus sobrinus*, for example.

The bacteriocins according to the present invention are characterized in greater detail below by means of various microbiological, biochemical and genetic data illustrating their properties. The percentages are given by weight.

Unit of antibacterial activity—"Agar Well-Test"

Within the framework of the present disclosure, antibacterial activity is defined in terms of arbitrary units.

One arbitrary unit (au) is defined as the reciprocal of the rate of the highest dilution at which a sample still exhibits antibacterial activity in the test known to persons skilled in the art under the name of "agar well test", the English expression which literally means a test using a well cut out in agar.

A standard sample of a supernatant of an *S. thermophilus* culture according to the present invention prepared under the standard conditions illustrated in Example 1, typically exhibits an activity of 32 au for a volume of 70 µl. This therefore means an activity of 460 au/ml.

A standard crude extract of bacteriocin, obtained from the culture supernatant illustrated in Example 1 by clarification followed by two successive precipitations with trichloroacetic acid each followed with a resuspension in aqueous suspension with trifluoroacetic acid, typically has an activity of about $1.4 \times 10^5$ au/ml.

It is with the aid of the agar well test that it is determined whether a sample still has an antibacterial activity at a given dilution rate.

In order to do this, 35 ml of M 17 medium are poured into a Petri dish and 1% sucrose and 1.5% agar are added thereto.

5 ml of M 17 medium to which 1% sucrose and 0.75% agar are added are inoculated with 5 µl of a culture, prepared during the previous night, of a strain of *S. thermophilus* which is typically sensitive to the present bacteriocin (typical indicator), in this case the strain Sfi3 for example.

The 5 ml are poured over the 35 ml and left to dry for 15 min under a laminar flow. Holes of 5 mm in diameter are punched in the culture medium.

The test samples are poured into the holes, in an amount of 70 µl per hole. The incubation is carried out for 6 h under anaerobic conditions at 42° C. During this incubation, the typical indicator strain has grown and inhibition halos are visible. The dilution rate at which a sample no longer exhibits antibacterial activity is the dilution rate from which an inhibition halo is no longer distinguished.

Inactivation by enzymes

With the aid of the agar well test, on agar inoculated with the typical indicator strain as described above, it is determined whether the present bacteriocins are inactivated or not by various enzymes.

For all the enzymes used except for lipase, 1 µg/ml to 10 mg/ml of enzyme is added to the standard crude extract diluted 33× in the buffer recommended by the enzyme supplier, so as to obtain samples of 70 µl at 300 au. The enzyme is then allowed to act for 30 min, at the temperature recommended by the supplier, before placing the whole in the well of the agar well test.

On the other hand, for the commercial lipase, 1 µl of a mixture of inhibitors (1.25M EDTA; 0.25% pepstatin A (p4265 Sigma); 0.25% E-64 (E3132 Sigma); 0.25% aprotinin (A1153 Sigma)) is first added to 100 µl of a solution comprising 200 µg/ml of lipase, the inhibitors are allowed to act for 45 min at room temperature, 5 µl (450 au) of diluted standard crude extract are then added and allowed to react for 30 min at 37° C., then 70 µl of the mixture are deposited in the well of the agar well test. The buffers used for the dilutions are the following.

pH 2.0: 100 mM maleic acid adjusted with NaOH,
pH 7.0: 100 mM phosphate buffer ($K_2HPO_4$/$KH_2PO_4$),
pH 7.5: 100 mM phosphate buffer ($K_2HPO_4$/$KH_2PO_4$),
pH 7.75: 100 mM Tris-Cl.

The diameter of the inhibition halo is compared with the control diameter of the halo obtained without addition of enzyme which, for each buffer and at each incubation temperature, is about 14 mm.

Table I below presents the results obtained with the tested enzymes. In this table, the enzyme is designated by its type, the name of the supplier and the item number of the supplier. The inactivation of the bacteriocin is indicated as a function of the concentration of the enzyme added. The figure 0 means that there is no longer any halo, in other words that the antibacterial activity of the present bacteriocin was impaired by the incubation with the enzyme. The figure 14 indicates that there is still a halo of 14 mm corresponding to the full antibacterial activity of the present bacteriocin.

TABLE I

| Enzymes | Concentration (µg/ml) | pH of the buffer | Incubation temperature (°C.) | Inactivation (mm) |
| --- | --- | --- | --- | --- |
| Pepsin (SIGMA P-700) | 10 | 2.0 | 37 | 0 |
| Proteinase K (MERCK 1000 144) | 4 | 7.0 | 37 | 0 |
| Ficin (SIGMA P-3266) | 10 | 7.0 | 37 | 0 |
| Pronase E (SIGMA P-8038) | 10 | 7.5 | 37 | 0 |
| Nagarse (SIGMA P-4789) | 10 | 7.5 | 37 | 0 |
| Trypsin (SIGMA T-8128) | 10 | 7.5 | 25 | 0 |

TABLE I-continued

| Enzymes | Concentration (μg/ml) | pH of the buffer | Incubation temperature (°C.) | Inactivation (mm) |
|---|---|---|---|---|
| α-chymotrypsin (SIGMA C-7762) | 1 | 7.75 | 25 | 0 |
| Catalase (SIGMA C-10) | 10000 | 7.75 | 25 | 14 |
| α-amylase (SIGMA λ-0521) | 1 | 7.75 | 25 | 14 |
| Lipase (SIGMA L-0382) + protease inhibitors | 200 | 7.75 | 37 | 14 |

All the proteases suppress the antibacterial activity of the supernatant, which demonstrates that a protein portion is involved in this activity.

The fact that no influence of catalase is observed on the antibacterial activity of the bacteriocins also demonstrates that the inhibition of the growth of the typical indicator strain is not due to the antibacterial activity of $H_2O_2$ which is known to have a similar activity to that of bacteriocins, since $H_2O_2$ would have been degraded by catalase.

Likewise, the fact that no inactivation of the antibacterial activity by α-amylase is observed demonstrates the absence of α-amylase-hydrolysable sugars involved in this antibacterial activity.

In addition, the fact that the lipase has no influence on the antibacterial activity also demonstrates the absence of a lipid fraction involved in this activity.

Inhibition spectrum

With the aid of the agar well test, on agar inoculated with various strains of spores or bacteria, it is determined whether the culture supernatant of the CNCM I-1351 strain producing the two bacteriocins according to the invention, has an inhibitory activity on the growth of these various bacteria, in other words, an inhibition spectrum is determined for this supernatant.

To do this, the inhibitory effect on the growth of the tested strain produced by a sample of supernatant exhibiting an activity of 300 au at pH 7.0 is observed in relation to the effect, which is normally zero, of the same sample previously deactivated by incubation at 37° C. for 30 min in the presence of 5 μg/ml of proteinase K.

To carry out these assays, FALCON 3046 Multiwell tissue culture plates are used. 6 ml of M17 medium containing, in addition, 1% lactose and 1.5% agar (M17L medium) is covered with 700 μl of M17 medium containing, in addition, 1% lactose and 0.6% agar inoculated with 1% of a culture of the test strain prepared during the previous night and diluted to an $OD_{600}$ of 0.1.

When the test strain has to grow from spores, the inoculation is carried out with $10^5$-$10^6$ spores per ml of covering medium.

When the test strain is not a Lactococcus, a Streptococcus or an Enterococcus, the M17L medium is replaced with a standard medium favourable to the growth of the bacterium in question, especially the MRS medium comprising, in addition, 2% glucose for Lactobacillus, Pediococcus, Leuconostoc and Bifidobacterium (Sanofi Diagnostics Pasteur, France), the RCM medium for the spores or vegetative cells of Clostridium (Oxoid, England), and the BHI medium (Difco, USA) for the other bacteria tested.

Two holes 5 mm in diameter and 5 mm deep are punched per plate. A 70 μl sample at 300 au of the present bacteriocin is placed in one of the holes, and in the other the same sample previously deactivated. The incubation is carried out at a temperature favourable to the growth of the tested strain for a period necessary for it to cover the plate with a visible bacterial lawn.

The effect or the degree of inhibition is characterized by the diameter of the inhibition halo observed. It is considered that the inhibition is very high (++++) if the halo has a diameter of 16–18 mm, high (+++) for a diameter of 11.5–15.5 mm, average (++) for a diameter of 7.5–11 mm, weak (+) for a diameter of 5–7.5 mm and zero (–) if no halo is observed.

More than 74 strains of lactic acid bacteria of various species and subspecies are thus tested and it is observed that only about 7% of them are resistant to the supernatant. The details of the result of these tests is presented in Table II below. In this Table II, as in the following tables, the strain name or No. indicated is the No. which is attributed to it in the Nestlé collection (address: NESTEC S. A., Research Centre, Vers-chez-les-Blanc, CH-1000 Lausanne 26, Switzerland). The temperature indicated is the incubation temperature during the test.

TABLE II

| Species | No. | T (°C.) | Inhibition |
|---|---|---|---|
| Streptococcus thermophilus | YS3 | 42 | +++ |
|  | YS4 | 42 | +++ |
| (The strains Sfi 12 and 25 | YS11 | 42 | +++ |
| exhibit resistance to the | YS7 | 42 | +++ |
| strain CNCM I-1351 and an | YS8 | 42 | +++ |
| anti-bacteria activity | YS20 | 42 | +++ |
| spectrum which is similar | Sfi3 | 42 | +++ |
| to this strain) | Sfi18 | 42 | +++ |
|  | Sfi19 | 42 | +++ |
|  | Sfi20 | 42 | +++ |
| (The strain STII exhibits | Sfi16 | 42 | +++ |
| resistance only to the | ST11 | 42 | – |
| strain CNCM I-1351; it | Sfi12 | 42 | – |
| appears however that less than 5% of streptococci are capable of expressing such a resistance) | Sfi25 | 42 | – |
| Lactococcus lactis | SL2 | 30 | ++ |
| (Nisine producers) | SL13 | 30 | ++ |
|  | SL16 | 30 | ++ |
|  | SL25 | 30 | ++ |
|  | SL31 | 30 | ++ |
|  | SL63 | 30 | ++ |
| Lactococcus lactis | SLP26 | 30 | ++ |
|  | SLP29 | 30 | ++ |
|  | SLP24 | 30 | ++ |
|  | SL64 | 30 | ++ |
|  | SL58 | 30 | ++ |
|  | SL40 | 30 | ++ |
| Lactococcus lactis biovar | SD39 | 30 | ++ |
| diacerylactis | SD80 | 30 | ++ |
|  | SD57 | 30 | ++ |
|  | SD11 | 30 | ++ |
|  | SD113 | 30 | ++ |
| Lactococcus cremoris | SC20 | 30 | ++ |
|  | SC15 | 30 | ++ |
|  | SC11 | 30 | ++ |
|  | SC145 | 30 | ++ |
|  | SC63 | 30 | ++ |
|  | SC28 | 30 | ++ |
| Enterococcus faecalis | SFS1 | 30 | + |

TABLE II-continued

| Species | No. | T (°C.) | Inhibition |
|---|---|---|---|
| | SFS2 | 30 | + |
| | SFS10 | 30 | + |
| Enterococcus faecium | SFM1 | 30 | ++ |
| | SFM3 | 30 | ++ |
| | SFM6 | 30 | ++ |
| | SFM10 | 30 | ++ |
| | SFM14 | 30 | ++ |
| | SFM9 | 30 | + |
| Lactobacillus fermentum | L26 | 30 | ++ |
| | L50 | 30 | ++ |
| | L28 | 30 | ++ |
| | LF16 | 30 | ++ |
| | LF15 | 30 | ++ |
| Lactobacillus helveticus | LH91 | 40 | ++++ |
| | LH2 | 40 | +++ |
| | LH3 | 40 | +++ |
| | LH1 | 40 | +++ |
| Lactobacillus acidophilus | LQ1 | 40 | ++ |
| | LQ3 | 40 | + |
| | LQ10 | 40 | ++ |
| | LQ21 | 40 | + |
| | LQ23 | 40 | ++++ |
| | LQ26 | 40 | − |
| Lactobacillus brevis | LB2 | 30 | +++ |
| | LB10 | 30 | − |
| | LB13 | 30 | +++ |
| Lactobacillus bulgaricus | YL12 | 40 | ++++ |
| | YL2 | 40 | + |
| | YL5 | 40 | ++ |
| | LB32 | 40 | +++ |
| Leuconostoc cremoris | LCC1 | 30 | ++ |
| | LCC7 | 30 | ++ |
| | LCC2 | 30 | ++ |
| Leuconostoc mesenteroides | LCM9 | 30 | ++ |
| | LCM10 | 30 | ++ |
| | LCM18 | 30 | ++ |

In this Table II, it is observed that the inhibition spectrum of the supernatant is narrow in the sense that for certain Lactobacillus species, such as Lactobacillus acidophilus, Lactobacillus brevis and Lactobacillus bulgaricus, for example, the degree of inhibition is heterogenous. However, for other species such as L. fermentum, L. helveticus and Lactococcus for example, the degree of inhibition is homogeneous.

This is advantageous in the light of the fact that it is very difficult to distinguish one strain from another within the same species. It is therefore possible to envisage an advantageous use of the supernatant or of the purified bacteriocins for distinguishing between industrial strains.

It is also possible to envisage the use of a strain producing at least one of the bacteriocins according to the present invention, in culture with another lactic acid bacterium strain which is naturally resistant, or slightly sensitive, to the bacteriocin(s) produced in the medium. Yogurts, especially yogurts exhibiting reduced post-acidification, for example, can thus be produced.

It is also observed that the supernatant inhibits the growth of the six nisin-producing strains of L. lactis. This proves that the present bacteriocin is not nisin. This is confirmed by the fact that the present bacteriocin is inactivated by trypsin at 10 μg/ml (cf. Table I), which is not the case for nisin.

However, the inhibition spectrum of the supernatant of a culture producing the two bacteriocins of the invention is also broad in the sense that it is not limited to species of lactic acid bacteria but that it extends to other species of Gram-positive bacteria, especially to the food bacteria Bifidobacterium, to the undesirable or pathogenic bacteria Propionibacterium, Listeria innocua, Listeria monocytogenes and Micrococcus varians, and to the spores and cells of numerous pathogenic bacteria of the genus Clostridium and Bacillus, for example, as demonstrated by the results presented in Table III below.

TABLE III

| Species | No. | T (°C.) | Inhibition |
|---|---|---|---|
| Bifidobacterium breve | BBR27 | 37 | +++ |
| | BBR4 | 37 | +++ |
| | BBR39 | 37 | +++ |
| Bifidobacterium longum | BL20 | 37 | +++ |
| | BL18 | 37 | +++ |
| | BL22 | 37 | +++ |
| Bifidobacterium bifidum | BB7 | 37 | +++ |
| | BB9 | 37 | +++ |
| | BB12 | 37 | +++ |
| Bifidobacterium infantis | B16 | 37 | +++ |
| | B11 | 37 | +++ |
| Propionibacterium | PP1 | 30 | +++ |
| Clostridium botulinum | CB1 | 30 | ++ |
| (Spores and vegetative cells) | CB2 | 30 | ++ |
| Clostridium tyrobutiricum | 107001 | 30 | + |
| (Spores and vegetative cells) | 107002 | 30 | ++ |
| Mixture of spores of | | | |
| Clostridium sporogenes | 100021 | | |
| Clostridium fermentum | 100022 | 30 | ++ |
| Clostridium butilinum | A-69; B-213; BKA40; B-73-211; | | |
| (6 strains) | A-80-124clovis; B-1-NCA | | |
| Listeria innocua | 24 | 30 | + |
| | 25 | 30 | + |
| | 27 | 30 | + |
| | 39 | 30 | + |
| | 40 | 30 | + |
| | 41 | 30 | + |
| Listeria monocytogenes | 57 | 30 | ++ |
| | 58 | 30 | ++ |
| | 59 | 30 | ++ |
| | 60 | 30 | ++ |
| | 61 | 30 | ++ |
| | 62 | 30 | ++ |
| Bacillus subitilis (spores and vegetative cells) | A2 | 30 | ++ |
| | A3 | 30 | ++ |
| | A13 | 30 | ++ |
| | A14 | 30 | ++ |
| | A15 | 30 | ++ |
| Bacillus pumilus (Spores and vegetative cells) | B2 | 30 | ++ |
| Bacillus cereus (spores and vegetative cells) | C14 | 30 | ++ |
| Micrococcus varians | MCV1 | 30 | ++ |
| Micrococcus luteus (nisin indicator) | MCL1 | 30 | − |

The results illustrated in this Table III make it possible, inter alia, to envisage advantageous uses of this supernatant or of the purified bacteriocins, as additive in the preparation of food products as active agent against pathogenic agents, especially in meat products against Clostridium, in cheeses against Listeria monocytogenes and C. tyrobutyricum, or in fresh pasta or sauces for fresh pasta against Bacillus from which the above strains indeed originate for example.

Finally, the present bacteriocins exert no inhibitory effect on the growth of Gram- bacteria, as can be observed in the light of the results illustrated in Table IV below.

TABLE IV

| Species | No. | T (°C.) | Inhibition |
|---|---|---|---|
| *Escherichis coli* | BZ234 | 37 | – |
| *Salmonella thyphimurium* | 274 | 37 | – |
| | 273 | 37 | – |
| *Pseudomonas aeruginosa* | 5 | 37 | – |
| | 13 | 37 | – |
| *Pseudomonas fluorescens* | 11 | 37 | – |
| | 12 | 37 | – |

Heat resistance, stability

The bacteriocins present in the extract obtained under the conditions illustrated in Example 1 do not exhibit good stability to preservation at 4° C. if the extract is not previously heated. On the other hand, they exhibit good stability to preservation if the extract is sharply heated for at least 15 min at 90°–121° C. for example.

It was checked in particular that more than 50% of the activity of such an extract is preserved after 5 months of preservation at 4° C. if the said extract was heated beforehand for 20 min at 94° C. on a water bath for example. It was also checked that 100% of the activity is preserved after heating the said extract for 60 min at 100° C. (test carried out on a thermostatted oil bath on 1 ml of the supernatant, concentrated or otherwise, of a culture of a strain of *S. thermophilus* according to the present process).

On the other hand, the present bacteriocins preserve only about a third of their activity after a sterilizing treatment of 30 min at 121° C. (test carried out on 40 ml of the non-concentrated supernatant of a culture of a strain of *S. thermophilus* according to the present process) for example.

Finally, by ultrafiltration tests on Amicon filters followed by gel electrophoresis (SDS-PAGE), it is observed that the bacteriocins of the present invention in the supernatant of a culture of *S. thermophilus*, especially in the supernatant of the standard culture obtained in Example 1, exist in the form of aggregates of molecular weight (MW) greater than 10 kDa, of which 67% exhibit a MW of less than 100 kDa at 33% exhibit a MW greater than 100 kDa.

Purification of the bacteriocins

In the description which follows, the percentages of trifluoroacetic acid and acetonitrile are given by volume.

1 litre of a culture of the CNCM I-1351 strain is produced in an M17 medium supplemented with 1% sucrose, for 6 h, at 42° C. and under anaerobic conditions.

20 g of XAD-7 resin (Sigma) are then added directly to the culture and the whole is stirred gently for 1 h at 4° C. The mixture is then filtered through a Schleicher & Schvell filter (Germany) No. 604, then the resin retained on the filter is washed with 1 litre of a 50 mM acetic acid solution pH 5.2, in order to remove the bacteria. The resin is then placed in a column and the bacteriocins are eluted with 45 ml of a solution comprising 70% acetonitrile and 0.1% trifluoroacetic acid (TFA). An eluate comprising both bacteriocins is then obtained.

These two eluted bacteriocins are then separated in the following manner.

The volume of eluate is first reduced to 24 ml by centrifugation/freeze-drying (Speedvac, Savant Instrument), the volume obtained is then adjusted to a concentration of 2M NaCl and 250 mM Tris.Cl, pH 8, to a volume of 50 ml, then this volume is injected into a Phenyl Superose HR 16/10 column with hydrophobic interaction (Pharmacia) previously equilibrated with a buffer comprising 50 mM Tris.Cl, pH 8 and 2M NaCl. 200 ml of the preceding buffer, 100 ml of a linear gradient starting with the preceding buffer and ending with a 50 mM Tris.Cl solution, pH 8, 100 ml of the preceding solution, 60 ml of pure water, 60 ml of 50 mM Tris.Cl solution, pH 8, and finally 60 ml of pure water are then passed successively at a rate of 4 ml/min.

50 µl of each fraction collected at the outlet of the column are then diluted in 50 µl of 0.1% TFA, then the antibacterial activity of each mixture is tested by the agar well test described above.

It is thus observed that the 470th to 490th ml fractions exhibit an antibacterial activity. These fractions are then mixed, the volume of this mixture is reduced by centrifugation/freeze-drying to 1 ml, then this reduced volume is injected into a Pep RPC HR 5/5 column (Pharmacia) previously equilibrated with a 0.1% TFA solution, called in this disclosure "solution A". A solution of elution "B" comprising 70% acetonitrile and 0.097% TFA is also prepared. 1 ml of solution A, 9 ml of a linear gradient starting with solution A and ending with a 50/50 mixture of solutions A and B, 2 ml of this latter mixture, 7 ml of a linear gradient starting with this latter mixture and ending with a second 20/80 mixture of solutions A and B, 2 ml of a linear gradient starting with this second mixture and ending with solution B, then 2 ml of this latter solution are then successively passed through the column at a rate of 1 ml/min.

The antibacterial activity of the fractions at the outlet of the column is then determined by the agar well test as described above. All the fractions from the 14th to the 22nd ml exhibit an antibacterial activity. On the other hand, two major protein peaks, observed at an optical density of 215 mn, are distinguished in fractions 15 and 21 (in millilitre).

Sequencing of the bacteriocins

The N-terminal part of the proteins contained in fractions 15, 18, 20, 21 and 22 is sequenced using an Applied Biosystems 4774 automatic sequencer.

The presence of a peptide having a sequence of 48 amino acids which is identical to that, for the N-terminal part, of the sequence SEQ ID NO: 1 is thus revealed in fraction 15. Another peptide predominantly present in fraction 21 also has a sequence of 23 amino acids which is identical to that, for the N-terminal part, of the sequence SEQ ID NO: 2.

These results therefore demonstrate that the strain CNCM I-1351 produces two peptides having an antibacterial activity. However, the different appearance of the inhibition halos obtained between fractions 15 and 21, makes it possible to suspect a different antibacterial activity between thermophilin 1 and thermophilin 2 of the present invention.

On the other hand, the amino acid composition of fractions 15 and 21, previously hydrolysed with 6N HCl, at 100° C. for 24 h, is analysed by the known method of "dabsyl chloride derivatization". The results show that the amino acid composition of each fraction already appears to correspond to their respective peptide sequence.

Finally, fractions 15 and 21 are also subjected to mass spectometry, and a molecular weight which is of the order of 5800 Dalton is revealed for thermophilin 1, and a molecular weight which is of the order of 3900 Dalton is revealed for thermophilin 2.

Sequencing of the genes for the bacteriocins

The degenerate nucleic sequences SEQ ID NO: 6 and SEQ ID NO: 7 described in the sequence listing below, which correspond respectively to the N-terminal part and the C-terminal part of the thermophilin 1 peptide sequenced previously, are manufactured in a conventional manner.

A portion of the mixture of SEQ ID NO: 6 sequences is then rendered radioactive by the action of T4 polynucleotide kinase as described in the laboratory manual "Molecular cloning, a laboratory manual" (second edition, Sambrook et al., Cold Spring Harbor, Laboratory Press, 1989), called in the present disclosure "Maniatis".

PCR ("polymerase chain reaction") is then carried out with the aid of the two non-radioactive mixtures of the degenerate sequences SEQ ID NO: 6 and SEQ ID NO: 7, on a chromosomal DNA preparation from the strain CNCM I-1351, as described in the manual "PCR techology" (H. A. Erdlich editor, M stockton press, London).

A band of 128 base pairs (pb) is then revealed on an electrophoresis gel, which is then eluted according to Maniatis. A portion is then cloned directly into the plasmid pGEM-T (Promega) following the recommendations of the supplier, and is then sequenced by the "dideoxynucleotide" method, according to Maniatis, using the universal pUC19 probes. A probe having the sequence SEQ-ID NO: 8 described in the sequence listing below, corresponding to a sequence encoding amino acids 9 to 47 of thermophilin 1, is thus obtained. Finally, the other portion of the eluted band of 128 pb is rendered radioactive by the method called "random priming" according to Maniatis.

On the other hand, a digestion of a chromosomal DNA preparation from the strain CNCM I-1351 is carried out with EcoRI and HindIII following the recommendations of the enzyme supplier, 10 µg of digestion product are then run on an analytical electrophoresis gel, the DNA is transferred in alkaline medium from the gel onto a "Zeta probe" membrane (Biorad), the membrane is prehybridized at 54° C. overnight in a medium comprising 6× SSC, 1% SDS and 1% skimmed milk, then this membrane is hybridized to the radioactive degenerate probe SEQ ID NO: 6 in the previous hybridization medium, first for 18 h at 54° C., decreasing the temperature by 2° C. every 3 h, then for 24 h at 42° C. The membrane is then washed for 2 min, three times in succession, in 6× SSC at room temperature, and for 1 min in 6× SSC at 47° C. The membrane is finally exposed to an autoradiography film. All these steps are carried out according to the Maniatis manual.

A 3.6 kb band is then revealed, which makes it possible for us to locate in a preparative electrophoresis gel of the chromosomal DNA (300 µg) of the strain CNCM I-1351 performed under the same conditions as described above, the gel portion comprising the piece of DNA which is of interest. This gel portion is then cut out and eluted in a conventional manner, and the eluted DNA is ligated to the vector pUC19 (Messing et al., Methods Enzymol., 101:20, 1983) previously hydrolysed with EcoRI and HindIII. These steps are carried out according to the Maniatis manual.

The strain BZ234 of *Escherichia coli* (Biocentre collection, University of Bâle, Switzerland) rendered competent beforehand, is then conventionally transformed with the ligation medium. The transformed cells are then selected by α-complementation. Then according to the method called "colony lift", according to Maniatis, 300 transformed colonies are transferred to a filter, they are lysed, they are hybridized to the radioactive sequence SEQ ID NO: 8, then the filter is exposed to an autoradiography film.

13 colonies having a plasmid capable of hybridizing with the sequence SEQ ID NO: 8 are then observed on the film. Two of these colonies are then selected, the plasmid DNA is conventionally extracted therefrom, and the DNA fragment cloned into the two selected pUC19 plasmids is sequenced by the "dideoxynucleotide" method, with the aid of universal pUC19 probes, then probes based on the sequences thus obtained.

A nucleic sequence SEQ ID NO: 3 described in the sequence listing below is thus obtained which is identical for the two plasmids selected. This sequence thus comprises an operon encoding two proteins having the amino acid sequences SEQ ID NO: 4 corresponding before maturation to thermophilin 1, and SEQ ID NO: 5 corresponding before maturation to thermophilin 2 (see the sequence listing below). A third open reading frame also starts from nucleotide 679 of this sequence, and should certainly correspond to the gene for immunity.

By comparing the N-terminal peptide sequences of the purified bacteriocins and the amino acid sequences of the proteins encoded by the coding frames of the operon SEQ ID NO: 3, it can be determined that the protein of amino acid sequence SEQ ID NO: 4 (thermophilin 1) has a leader peptide of 23 amino acids which has a Glycine-Glycine unit characteristic of a class of bacteriocins from lactic acid bacteria. Finally, the molecular mass of thermophilin 1, calculated from its nucleic sequence, corresponds to that found by spectrometry, that is to say is of the order of 5800 Dalton.

Likewise, the protein of amino acid sequence SEQ ID NO: 5 (thermophilin 2) has a leader peptide of 21 amino acids, which has a Glycine-Glycine unit characteristic of a class of bacteriocins from lactic acid bacteria. Finally, the molecular mass of thermophilin 2, calculated from its nucleic sequence, corresponds to that found by spectrometry, that is to say is of the order of 3900 Dalton.

Role of the different bacteriocins

A homology with the first peptide of the "lactococein M" operon (Klaenhammer et al., FEMS Micro. Rew., 12, 39–86, 1993) was found for the sequence of thermophilin 1. This homology relates to the repetition of a GA unit. Likewise, a homology with a gene for the "lactacin F" operon (Klaenhammer et al., cited above) was found for thermophilin 2, in the GenEMBL data bank using the TFASTA program from GCG.

The two lactococein M and lactacin F operons in fact encode poration complexes involving several peptides. It is therefore possible that the operon previously described can encode peptides acting conjointly in a poration complex.

Nevertheless, it is not excluded that the two bacteriocins act independently, because of the somewhat different inhibition halo observed between the two thermophilins in the agar well test previously described.

EXAMPLES

The examples below are presented as illustration of the process of production and of the uses of the bacteriocin according to the present invention. The percentages are given therein by weight unless where stated otherwise.

Example 1

An M17 culture medium to which 1% sucrose has been added is inoculated with 1% (v/v) of a culture conaining $10^8$ microorganisms of the strain CNCM I-1351 of *S. thermophilus* per ml. The incubation is carried out for 6 h at 42° C. under anaerobic conditions after which the medium contains about $10^8$ microorganisms of the strain per ml and has an $OD_{600}$ of 3.6.

The standard culture thus obtained is centrifuged. The supernatant (standard) is collected. It is acidified to pH 1.5 with $H_3PO_4$, a precipitate is obtained which is removed by centrifugation and an acidic precipitation supernatant is collected.

The bacteriocins contained in the latter are precipitated with 10% trichloroacetic acid. The precipitated bacteriocins are collected and thereafter resuspended in aqueous suspension with 0.2% trifluoroacetic acid (v/v).

The bacteriocins are reprecipitated with 10% trichloroacetic acid. The precipitated bacteriocins are collected, they are washed with 100% acetone and they are resuspended in aqueous suspension with 0.2% trifluoroacetic acid (v/v).

A standard crude extract of the present bacteriocins is obtained having an activity of $1.4 \cdot 10^5$ au/ml.

Table VI below gives some details on the characteristics of one litre of standard supernatant and on those of the 18 ml of standard crude extract, in other words of concentrate which was obtained therefrom, especially in terms of protein content and antibacterial activity.

TABLE V

|  | Volume (ml) | Total protein (PIERCE kit) (mg) | au/ml | au/mg protein | au/mg dry weight | Total activity (au) |
| --- | --- | --- | --- | --- | --- | --- |
| Supernatant | 1000 | 6700 | $4.6 \times 10^2$ | 68 | — | $4.6 \times 10^3$ |
| Crude extract | 18 | 83 | $1.4 \times 10^5$ | $2.5 \times 10^5$ | $1.4 \times 10^5$ | $2.1 \times 10^6$ |

Example 2

Set-style yogurts are prepared comprising the strain of the invention *S. thermophilus* CNCM I-1351, and the strains ST11 of *S. thermophilus* (which is resistant to the bacteriocins according to the invention but exhibiting no antibacterial activity) and YL5 of *L. bulgaricus* mentioned above.

A milk based on whole milk comprising 3.7% fat and 2.5% skimmed milk powder is thus prepared. 40 l of this milk are pasteurized at 92° C. for 6 min, it is then homogenized at 75° C. and 150 bar (two stages), finally it is cooled to a temperature of about 42° C.

The freeze-dried strains *S. thermophilus* CNCM I-1351, *S. thermophilus* ST11 and *L. bulgaricus* YL5 are then reactivated by several successive precultures in a sterile MSK medium (10% reconstituted powdered skimmed milk comprising 0.1% of a commercial yeast extract).

The sterile milk is then inoculated in an amount of 1% (v/v) of the third preculture of each *S. thermophilus* strain taken at the stage for coagulation of the medium, and in an amount of 2% (v/v) of the third preculture of the *L. bulgaricus* strain taken at the stage for coagulation of the medium. The milk is then incubated at 42° C. up to a pH of about 4.65, then it is cooled to 4° C.

For comparison, a traditional set-style yogurts is prepared in the same manner as described above, with the previously described strains YS8 and SFi3 of *S. thermophilus*, and the strain YL18 of *L. bulgaricus*, which are traditionally used for the manufacture of yoghurt.

Table VI below illustrates the characteristics of the products obtained, especially their pH during their preservation at 4° C.

TABLE VI

| Examples | Time for acidification up to pH 4.65 | pH of the product after 1 day (at 4° C.) | pH of the product after 24 days (at 4° C.) |
| --- | --- | --- | --- |
| Example 2 | 8 h 30 | 4.6 | 4.6 |
| Comparative example | 6 h | 4.34 | 4.3 |

Example 3

Mozzarella cheese is prepared in a traditional manner with the aid of an *S. thermophilus* CNCM-1351 culture.

Example 4

10 litres of a culture of the strain CNCM I-1351 of *S. thermophilus* are produced in an M17 medium supplemented with 1% sucrose, for 6 h, at 42° C. and under anaerobic conditions. 200 g of XAD-7 resin (Sigma) are then added directly to the culture, the whole is stirred gently for 1 h at 4° C. The mixture is then filtered through a Schleicher & Schuell filter (Germany) No. 604, then the resin retained on the filter is washed with 10 litres of a 50 mM acetic acid solution, pH 5.2, in order to remove the bacteria. 450 ml of a solution comprising 100% ethanol and 20 mM ammonium acetate are then added to the resin, the whole is filtered in order to remove the resin, then the filtrate is freeze-dried until a powder comprising the bacteriocins according to the invention is obtained which can be used in the food industry.

The antibacterial activity of this powder, previously diluted in water, is then determined by the agar well test described above. This powder exhibits $10^7$ au/g of powder.

Finally, 0.5 g/kg of the above powder is added to a meat mousse during its preparation in a traditional manner. A meat mousse is thus obtained comprising $5.10^3$ au/g of bacteriocins capable of completely inhibiting the development of pathogenic bacteria, especially Clostridium.

Example 5

This example relates to the preparation of a moisturizing cream for skin care containing 0.05 g/kg of the powder described in Example 4, that is to say therefore $5 \cdot 10^2$ au/g of bacteriocins capable of inhibiting the development of undesirable bacteria on the skin.

To manufacture this emulsion, the components of the lipid phase A are mixed and it is heated to 75° C. The aqueous phase B is prepared and it is also heated to 75° C., then it is added to the lipid phase A while mixing slowly, and the mixture is then cooled, with slow mixing, to room temperature, that is to say about 25° C. At this temperature, the constituents C are slowly added in the order of the formula.

| Lipid Phase A | |
|---|---|
| | % |
| Peg-6-stearate, glycerate and peg-20-cethyl ether (peg:polyethylene glycol) | 15 |
| Vaseline oil | 5 |
| Wheat germ oil stabilized with 0.1% phenylindans (antioxidant) and 1% soya bean phospholipids (see EP94109355.1) | 3 |
| Sweet almond oils | 2 |
| Cetyl alcohol | 1 |
| Isostearyl isostearate | 2 |
| 2-Octyl-dodecyl-myristate | 1 |
| Lanolin wax | 1 |

| Aqueous Phase B | |
|---|---|
| | % |
| Methylisothiazoline | 0.1 |
| Demineralized water | 59.6 |
| Human placenta protein | 2 |

| Additives C | |
|---|---|
| | % |
| Propylene glycol and calendula extract | 2 |
| 50% soluble collagen in demineralized water | 5.8 |
| Perfume | 0.3 |
| 2.5% bacteriocin powder according to Ex. 4 in demineralized water | 0.2 |

Example 6

0.5 g/kg of the bacteriocin powder described in Example 4 is added to a liquid dentifrice. This dentifrice is thus capable of inhibiting the development of pathogenic bacteria of the buccal cavity, and especially *Streptococcus sobrinus*.

Example 7

A solution comprising the bacteriocin powder of Example 4 diluted in water in an amount of 1%, is sprayed on a food product intended to be sterilized in order to prevent post-contamination during packaging.

What is claimed is:

1. An isolated *streptococcus thermophilus* bacteriocin having the amino acid sequence SEQ ID NO: 1 or SEQ ID NO: 2.

2. A process for preparing a food or cosmetic product which comprises adding at least one bacteriocin according to claim 1 to the product in an amount effective to impart antibacterial activity to the product.

3. The process of claim 2 wherein the bacteriocin is added in the form of an extract which is obtained by culturing a *Streptococcus thermophilous* strain in a medium under conditions favorable to the growth of the strain to form a culture which contains about $10^7$ to $10^9$ microorganisms of the strain per ml, centrifuging the culture to produce a supernatant which contains the bacteriocin, and obtaining the extract from the supernatant.

4. The process of claim 2 wherein the bacteriocin is added by incorporating a *Streptococcus thermophilous* strain in the product.

5. The process of claim 4 wherein a culture of the *Streptococcus thermophilous* strain is used as a starter in the preparation of a cheese or acidified milk product.

6. The process of claim 4 wherein the strain is CNCM I-1351.

7. The process of claim 2 wherein the product is a meat product, a cream, a lotion or an oral health product and the bacteriocin is present in the product in an amount effective against pathogenic bacteria.

* * * * *